US008858882B2

(12) United States Patent  
Adachi et al.

(10) Patent No.: US 8,858,882 B2  
(45) Date of Patent: Oct. 14, 2014

(54) AUTOMATIC ANALYSIS DEVICE (75) Inventors: Sakuichiro Adachi, Hitachinaka (JP); Terumi Tamura, Hitachinaka (JP); Hajime Yamazaki, Hitachinaka (JP); Akihisa Makino, Hitachinaka (JP); Takeshi Yogi, Higashimurayama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/577,963

(22) PCT Filed: Feb. 24, 2011

(86) PCT No.: PCT/JP2011/054067  
§ 371 (c)(1),  
(2), (4) Date: Aug. 9, 2012

(87) PCT Pub. No.: WO2011/105464  
PCT Pub. Date: Sep. 1, 2011

(65) Prior Publication Data  
US 2012/0315190 A1 Dec. 13, 2012

(30) Foreign Application Priority Data

Feb. 25, 2010 (JP) ................. 2010-039800

(51) Int. Cl.  
*G01N 21/75* (2006.01)  
*G01N 21/51* (2006.01)  
*G01N 35/02* (2006.01)  
*G01N 21/53* (2006.01)

(52) U.S. Cl.  
CPC .............. *G01N 21/51* (2013.01); *G01N 35/025* (2013.01); *G01N 21/532* (2013.01)  
USPC ................... 422/67; 422/64; 422/65; 422/63; 435/288.7; 436/47

(58) Field of Classification Search  
CPC ....... G01N 21/51; G01N 35/025; G01N 35/04; G01N 35/026; G01N 2030/8804; G01N 2201/0415; G06T 5/002; G06K 9/40; G01F 23/292; G01F 23/2966  
USPC .............. 422/63–67, 68.1; 435/288.7; 436/47  
See application file for complete search history.

(56) References Cited

U.S. PATENT DOCUMENTS 4,265,535 A 5/1981 Pitt  
4,420,257 A 12/1983 Fukuda et al.  
(Continued)

FOREIGN PATENT DOCUMENTS

GB 2 105 028 3/1983  
JP S63 205546 A 8/1988  
(Continued)

OTHER PUBLICATIONS

Journal of China Coal Society, vol. 32, No. 6, Jun. 2007, pp. 606, Item 3.2.

(Continued)

*Primary Examiner* — Shogo Sasaki  
(74) *Attorney, Agent, or Firm* — Antonelli, Terry, Stout & Kraus, LLP.

(57) ABSTRACT

There is provided a data processing method that reduces influences of air bubbles and dirt while maintaining changes in light amounts. Two scattering light photoreceivers are disposed in the forward direction. A photoreceiver 33a closer to the optical axis is taken to be a main angle photoreceiver, and a photoreceiver 33b further from the optical axis is taken to be a sub-angle photoreceiver. Noise is estimated based on the reaction process data of the sub-angle photoreceiver, and noise is reduced by subtracting the estimated noise from the reaction process data of the main angle photoreceiver.

4 Claims, 4 Drawing Sheets

(56) References Cited

U.S. PATENT DOCUMENTS

| | | | |
|---|---|---|---|
| 4,451,433 A | 5/1984 | Yamashita et al. | |
| 4,674,879 A | 6/1987 | Gregorig et al. | |
| 6,791,676 B1 | 9/2004 | Meller | |
| 2002/0042142 A1 | 4/2002 | Kawamura | |
| 2003/0087289 A1* | 5/2003 | Zuzan et al. | 435/6 |
| 2003/0124589 A1* | 7/2003 | Piper | 435/6 |
| 2008/0285025 A1 | 11/2008 | Adachi | |
| 2009/0180120 A1 | 7/2009 | Kanayama | |

FOREIGN PATENT DOCUMENTS

| | | |
|---|---|---|
| JP | 1-295134 | 11/1989 |
| JP | 9-273987 | 10/1997 |
| JP | 10-332582 | 12/1998 |
| JP | 2000-065744 | 3/2000 |
| JP | 2002-116145 | 4/2002 |
| JP | 2002-250692 | 9/2002 |
| JP | 2005-049109 A | 2/2005 |
| JP | 2007-322324 | 12/2007 |
| JP | 2008-8794 | 1/2008 |
| JP | 2008-286567 | 11/2008 |
| JP | 2009-186461 | 8/2009 |
| JP | 2001-141654 | 5/2011 |
| WO | WO 2006/124673 | 11/2006 |
| WO | WO 2008/038329 | 4/2008 |

OTHER PUBLICATIONS

Supplementary European Search Report for Application No. EP 1174 7424 dated Apr. 23, 2014.

* cited by examiner

AUTOMATIC ANALYSIS DEVICE

TECHNICAL FIELD

The present invention relates to an auto analyzer that analyzes component amounts contained in a sample, e.g., an auto analyzer that analyzes component amounts contained in blood or urine.

BACKGROUND ART

As auto analyzers that analyze component amounts contained in a sample, devices that irradiate a sample, or a reaction solution in which a sample and a reagent are mixed, with light from a light source, measure the amount of transmitted light with respect to a single wavelength or a plurality of wavelengths obtained as a result to calculate the absorbance, and determine component amounts based on the relationship between absorbance and density in accordance with the Lambert-Beer law are used widely (e.g., Patent Literature 1). In such devices, numerous cells holding a reaction solution are arranged along the circumference of a cell disk that alternates between rotating and being stationary, and, while the cell disk is rotating, a data series of changes in the amount of light at given points in time (reaction process data) is measured as changes in the amount of received light over time for approximately ten minutes at regular time intervals by a transmitted light measuring unit disposed at a predetermined position.

Auto analyzers measure, as reactions of reaction solutions, two broad categories of reactions, namely color reactions between a substrate and an enzyme, and agglutination reactions between an antigen and an antibody. The former relate to biochemical assays which may be used to test for LDH (lactate dehydrogenase), ALP (alkaline phosphatase), AST (aspartate oxoglutarate aminotransferase), etc. The latter relate to immunoassays which may be used to test for CRP (C-reactive protein), IgG (immunoglobulin G), RF (rheumatoid factor), etc. Some substances measured by the latter immunoassays are found in blood in low concentrations, and thus require high sensitivity. For such substances, a reagent in which the surfaces of latex particles are sensitized (bound) with antibodies is used, and, as a component contained in the sample is recognized and agglutination is caused, the reaction solution is irradiated with light to measure the amount of light transmitted without being scattered by the latex clumps, thereby determining the amount of the component contained in the sample.

With respect to the above, there have been attempts to enhance sensitivity by measuring the amount of scattering light, instead of measuring the amount of transmitted light as is done in ordinary analyses. By way of example, there have been disclosed: a system in which transmitted light and scattering light are separated using a diaphragm, and absorbance and scattering light are simultaneously measured (Patent Literature 2); a feature whereby precision on the high-concentration side is enhanced by measuring reflected scattering light caused by large clumps that are formed as an agglutination reaction progresses (Patent Literature 3); a method in which integrating spheres are placed in front of and behind a reaction container, the respective average light amounts of forward scattering light and back scattering light are measured, and changes in turbidity caused by cell misalignment are corrected (Patent Literature 4); a method that provides for easier device size reduction and device adjustment by disposing a fluorescence/scattering light measurement detection system in the same plane as the cell rotation direction (Patent Literature 5); a turbidity measuring method in which turbidity is calculated based on the ratio between scattering light intensity and transmitted light intensity with respect to particles flowing in a flow cell (Patent Literature 6); etc.

CITATION LIST

Patent Literature

Patent Literature 1: U.S. Pat. No. 4,451,433
Patent Literature 2: JP 2000-307117 A
Patent Literature 3: JP 2008-8794 A
Patent Literature 4: JP 10-332582 A (1998)
Patent Literature 5: JP 1-295134 A (1989)
Patent Literature 6: JP 9-273987 A (1997)

SUMMARY OF INVENTION

Technical Problem

With respect to photometers that utilize scattering light, no efforts have hitherto been made to enhance sensitivity through the processing of reaction process data. Although Patent Literature 2 may enable scattering light and transmitted light to be measured simultaneously, there is no disclosure regarding any data processing method. Although scattering light is obtained in Patent Literature 3, this is done to improve precision on the high-concentration side, and it is ineffective for enhancing sensitivity for low concentrations. Patent Literature 4 averages scattering light with the integrating spheres, which does not result in enhanced sensitivity. Further, the system performs measurement while the cells are stationary. While Patent Literature 5 relates to a turbidity measuring method in which turbidity is calculated based on the ratio between scattering light intensity and transmitted light intensity, there is no disclosure of a specific processing method.

In order to enhance sensitivity, it is important that signals (changes in light amount) increase, and noise decrease, in the reaction process. In general, data processing methods that are effective with respect to noise vary depending on the main cause thereof. If random noise is the main cause, a process in which light amounts measured with a plurality of photoreceivers are averaged is effective, whereas if air bubbles, dirt, etc., are the main cause, a process in which the ratio or difference among light amounts measured with a plurality of photoreceivers is determined is effective.

Since auto analyzers take measurements while cells are rotating, it becomes important to secure a light amount with which sufficient measurement precision may be maintained even in short periods of time. In scattering light measurement, since the latex clumps and the wavelength are on approximately the same order of size, it falls into the realm of Mie scattering, which is advantageous in terms of securing light amounts since the amount of scattering light is large in the forward direction. In order to measure forward light, only light that has traveled through a square transmitting surface of a cell is to be measured, and light must be received at an angle that prevents entry of light that has traveled through the bottom surface of the cell or the solution surface. To that end, it is preferable that scattering light at an angle of approximately 35° or less relative to the optical axis be received. In auto analyzers, the latter air bubbles, dirt, etc., often become causes of noise. In ordinary transmitted light measurement, influences of air bubbles and dirt are eliminated by determining the ratio or difference among light amounts of numerous wavelengths. However, in the case of scattering light measurement, it is speculated that it is advantageous to determine the light amount ratio or difference among numerous angles. However, there was a problem in that, when a plurality of photoreceivers are disposed in such a manner as to receive scattering light at angles of 35° or less relative to the optical axis, and the ratio or difference of reaction process data among these plurality of photoreceivers are obtained as new reaction process data, signals drop and sensitivity does not improve because there is little difference among the light amounts, or the changes in light amount, thereof. As such, there is demand for a data processing method that improves sensitivity by determining the ratio or difference among light amounts without causing signals to drop.

Solution to Problem

In the present invention, in determining the ratio or difference between light amounts received by two scattering light photoreceivers disposed in the forward direction, the reaction process data received at one of the photoreceivers is corrected with estimated noise estimated from the reaction process data received at the other photoreceiver, thereby reducing noise. In particular, where, of the two scattering light photoreceivers, the photoreceiver closer to the optical axis is taken to be a main angle photoreceiver, and the photoreceiver farther from the optical axis is taken to be a sub-angle photoreceiver, noise is reduced by subtracting from the reaction process data of the main angle photoreceiver the estimated noise estimated from the reaction process data of the sub-angle photoreceiver. Both the main angle photoreceiver and the sub-angle photoreceiver are, in practice, disposed at positions for receiving scattering light whose scattering angles are greater than 0° but equal to or less than 35°.

More specifically, reaction process data $A(t, y_{at})$ of the main angle photoreceiver is approximated with fitting function $f_a(t)$, and reaction process data $B(t, y_{bt})$ of the sub-angle photoreceiver is approximated with fitting function $f_b(t)$. Sensitivity ratio $\alpha$ between the main angle photoreceiver and the sub-angle photoreceiver is assumed to be the ratio of gradients $f_a'(t)$ to $f_b'(t)$ of $f_a(t)$ and $f_b(t)$, respectively, indicated below.

$$\alpha = f_a'(t)/f_b'(t)$$

Residual error $r_b(t)$ as the difference between data value $y_{bt}$ and fitting function $f_b(t)$ of the sub-angle photoreceiver at reaction time t is defined as follows.

$$r_b(t) = y_{bt} - f_b(t)$$

Estimated noise n(t) at reaction time t is defined as follows in terms of sensitivity ratio $\alpha$ and residual error $r_b(t)$.

$$n(t) = \alpha \cdot r_b(t)$$

Noise corrected reaction process data $C(t, y_{ct})$ is obtained using data value $y_{ct}$, which is calculated by subtracting estimated noise n(t) from reaction process data value $y_{at}$ of the main angle photoreceiver.

$$y_{ct} = y_{at} - n(t)$$

A component amount in the sample is determined using this noise corrected reaction process data. Fitting functions $f_a(t)$ and $f_b(t)$ above may be linear functions, or other functions may be used.

Further, given how changes in light amount have opposite directionalities between transmitted light and scattering light (as the amount of scattering light increases, the amount of transmitted light decreases), a data processing method is indicated below for a case where the sub-angle photoreceiver is disposed in the 0°-direction, which coincides with the optical axis of the irradiating light. In this case, by determining the difference between the reaction process data of the scattering light photoreceiver and the reaction process data of the transmitted light photoreceiver, signals are amplified.

Specifically, assuming that $A(t, y_{at})$ is the reaction process data for scattering light, and that $D(t, y_{dt})$ is the reaction process data for transmitted light, then transmitted light corrected reaction process data $E(t, y_{et})$ is given by $$y_{et} = y_{at} - y_{dt}$$

Using this transmitted light corrected reaction process data, a component amount in the sample is determined. Thus, signals may be amplified, which is advantageous for enhancing sensitivity. In this case, too, the photoreceiver that receives scattering light is, in practice, disposed at a position for receiving scattering light whose scattering angle is greater than 0° but equal to or less than 35°.

Advantageous Effects of Invention

With the present invention, through data processing using reaction process data of two scattering light photoreceivers, noise caused by air bubbles and dirt is reduced, thereby enabling high-sensitivity measurement.

DESCRIPTION OF EMBODIMENTS

Embodiments of the present invention are described below with reference to the drawings.

Embodiment 1

A description is provided taking as an example a case where a main angle photoreceiver is disposed at a scattering angle of 20° and a sub-angle photoreceiver at a scattering angle of 30°.

Figure 1:
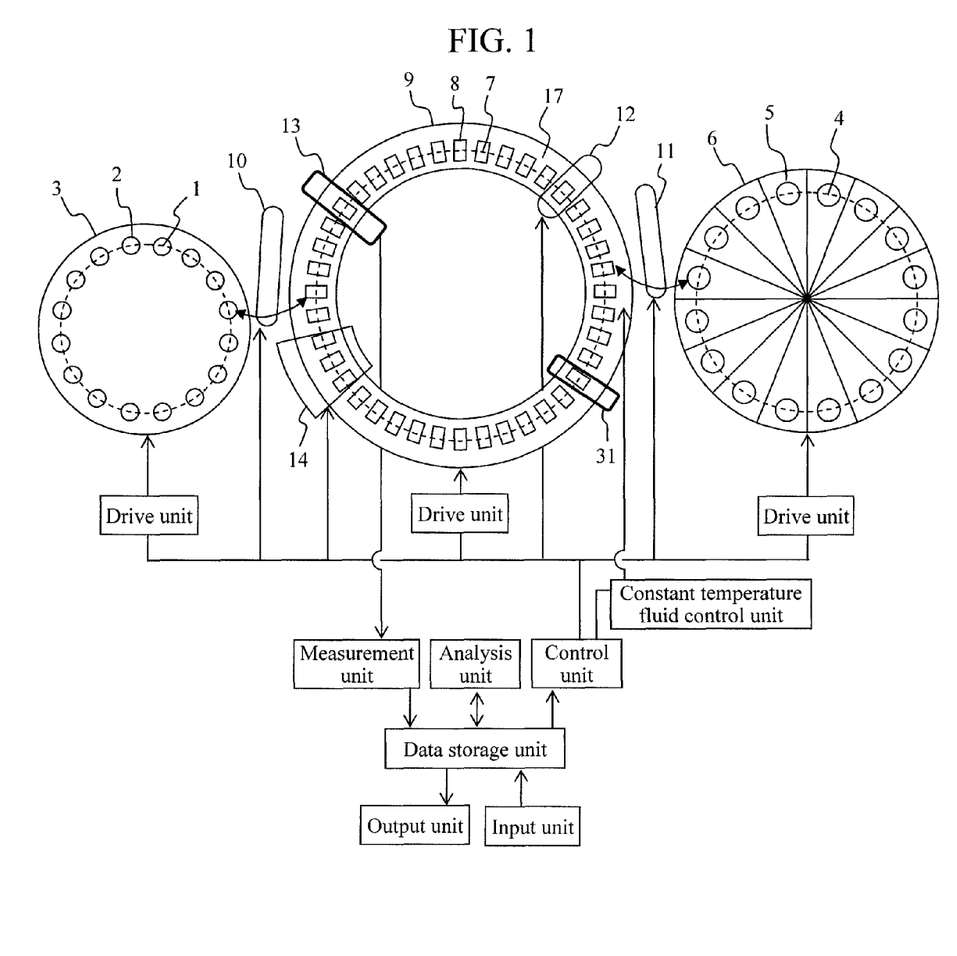
FIG. 1 is a schematic view showing an overall configuration example of an auto analyzer according to the present invention.

FIG. 1 is a schematic view showing an overall configuration example of an auto analyzer according to the present invention. This auto analyzer is equipped with a scattering light measuring unit for enhancing sensitivity. The auto analyzer mainly comprises: three types of disks, namely a sample disk 3, a reagent disk 6, and a cell disk 9; dispensing mechanisms for moving samples and reagents among these disks; a control unit that controls the above; a measurement unit; an analysis unit that processes measured data; a data storage unit that stores control data, measurement data, and analysis data; and an input unit and an output unit for inputting/outputting data to/from the data storage unit.

A plurality of sample cups 2 each containing a sample 1 are disposed along the circumference of the sample disk 3. A plurality of reagent bottles 5 each containing a reagent 4 are disposed in the reagent disk 6. A plurality of cells 8 in which the sample 1 and the reagent 4 are to be mixed to obtain a reaction solution 7 are disposed along the circumference of the cell disk 9. A sample dispensing mechanism 10 moves a given amount of the sample 1 from the sample cups 2 to the cells 8. A reagent dispensing mechanism 11 moves a given amount of the reagent 4 from the reagent bottles 5 to the cells 8. A stirring unit 12 stirs and mixes the sample 1 and the reagent 4 within the cells 8. A washing unit 14 discharges the reaction solution 7 from the cells 8 whose analyses have been completed and washes them. With respect to the washed cells 8, the next sample 1 is dispensed from the sample dispensing mechanism 10 again, and a new reagent 4 is dispensed from the reagent dispensing mechanism 11, and they are thus used for another reaction. The cells 8 are immersed in a constant temperature fluid 17 in a constant temperature bath whose temperature and flow rate are controlled, and the cells 8, as well as the reaction solution 7 therein, are moved while being kept at a constant temperature. Water is used for the constant temperature fluid 17, and the temperature and flow rate of the constant temperature fluid are controlled at a constant temperature fluid control unit. The temperature is regulated at the reaction temperature, namely 37° C.±0.1° C. A transmitted light measuring unit 13 and a scattering light measuring unit 31 are each provided at some part along the circumference of the cell disk. The transmitted light measuring unit 13 and the scattering light measuring unit 31 each irradiate the reaction solution in the cells with light from a light source and measure light that has interacted with the reaction solution.

The transmitted light measuring unit 13 irradiates the moving cells with light from a halogen lamp light source, and, after dispersion with a diffraction grating, receives the transmitted light with a photodiode array in which photodiodes are arranged in an array.

Figure 2:
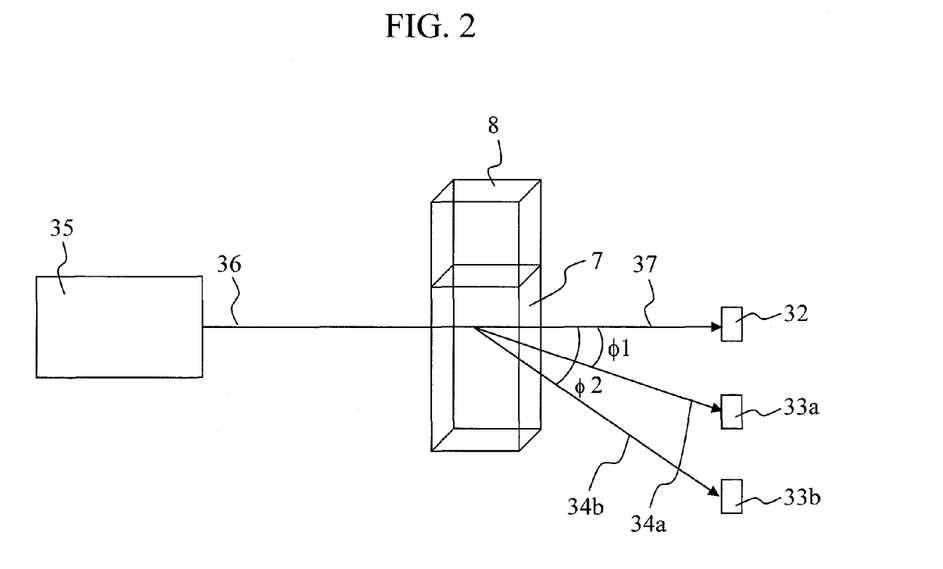
FIG. 2 is a schematic view of a scattering light measuring unit according to the present invention.

A schematic of the scattering light measuring unit 31 is shown in FIG. 2. The moving cells 8 are irradiated with irradiating light 36 from an LED light source 35, and transmitted light 37 is received with a transmitted light photoreceiver 32. In addition, main scattering light 34a and sub-scattering light 34b are measured with scattering light photoreceivers 33a and 33b, respectively. The main scattering light 34a and the sub-scattering light 34b are removed from the optical axis of the transmitted light 37 by scattering light reception angles φ1 and φ2, respectively. In the present embodiment, φ1 and φ2 were 20° and 30°, respectively. For the LED light source 35, L660-02V with an irradiating light wavelength of 660 nm, manufactured by Epitex, was used. Although, in this case, scattering light photoreceivers were disposed at 20°- and 30°-positions, optical systems, such as fibers and lenses, may instead be disposed at the same positions to guide light to scattering light photoreceivers disposed elsewhere. Although an LED was used for the light source 35, it may also be a laser, a xenon lamp, or a halogen lamp.

The analysis of the component amounts in the sample 1 is performed in the following steps. First, a given amount of the sample 1 in the sample cups 2 is dispensed into the cells 8 by the sample dispensing mechanism 10. Next, a given amount of the reagent 4 in the reagent bottles 5 is dispensed into the cells 8 by the reagent dispensing mechanism 11. When thus dispensing, the sample disk 3, the reagent disk 6 and the cell disk 9 are driven to rotate by their respective drive units under the control of the control unit, and the sample cups 2, the reagent bottles 5, and the cells 8 are moved in time with the dispensing mechanisms. Next, the sample 1 and the reagent 4 in the cells 8 are stirred by the stirring unit 12, and the reaction solution 7 is obtained. FIG. 1 is a schematic view, and shows one each of the reagent disk and the reagent dispensing mechanism. However, there typically are two reagent disks, reagent dispensing mechanisms, and stirring units. The transmitted light and scattering light from the reaction solution 7 are measured each time they pass through measurement positions of the transmitted light measuring unit 13 and the scattering light measuring unit 31 while the cell disk 9 is rotating, and are sequentially accumulated as reaction process data in the data storage unit via the measurement unit. After measuring light for approximately 10 minutes, the insides of the cells 8 are washed by the washing mechanism 14, and the next analysis is performed. In the mean time, if necessary, another reagent 4 is additionally dispensed into the cells 8 by the reagent dispensing mechanism 11, stirring is carried out by the stirring unit 12, and further measurements are taken for a given period of time. Thus, reaction process data for the reaction solution 7 with a given time interval are stored in the data storage unit. With the accumulated reaction process data, component amounts are analyzed at the analysis unit based on calibration curve data per test item. The data required for the control and analyses of the various units is inputted to the data storage unit from the input unit. In addition, the calibration curve data is held in the data storage unit. Various data, results, and alarms are outputted via display, etc., by the output unit.

In the present embodiment, a CRP reagent (nanopia CRP, manufactured by Sekisui Medical Co., Ltd.) was used for the latex item, and CRP Calibrator (manufactured by Sekisui Medical Co., Ltd.) 0.005 mg/dL concentration was used for the sample. After dispensing and stirring, the amount of light of the reaction solution was measured at the scattering light measuring unit 31 every five seconds for five minutes. Component amounts were determined from the measured reaction process data.

Figure 3A:
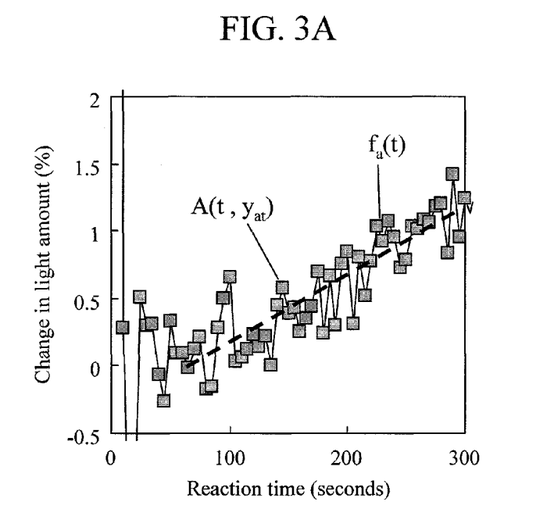
FIG. 3A is a chart showing reaction process data by a main angle photoreceiver with respect to Embodiment 1.
Figure 3B:
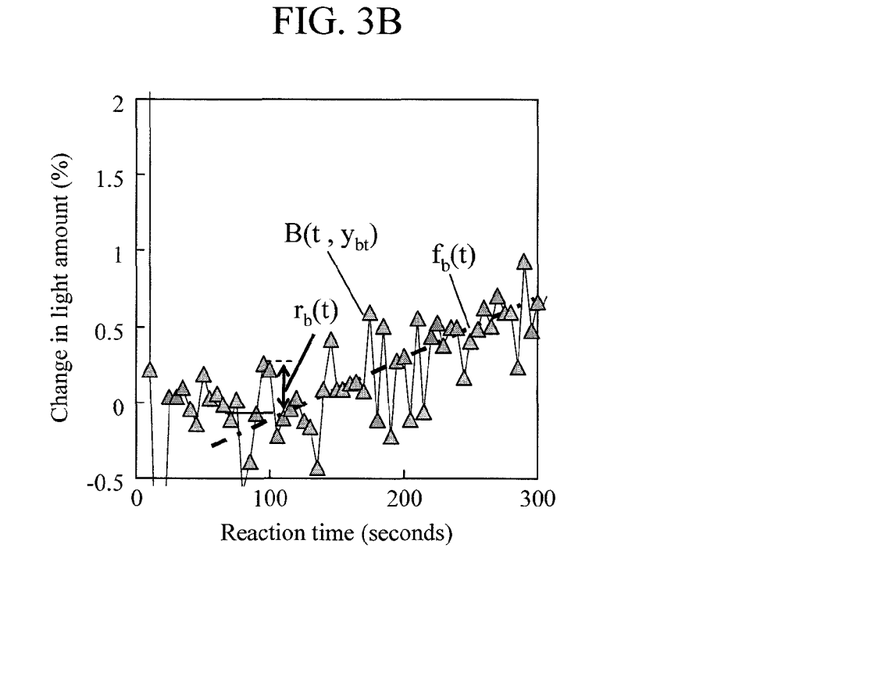
FIG. 3B is a chart showing reaction process data by a sub-angle photoreceiver with respect to Embodiment 1.
Figure 3C:
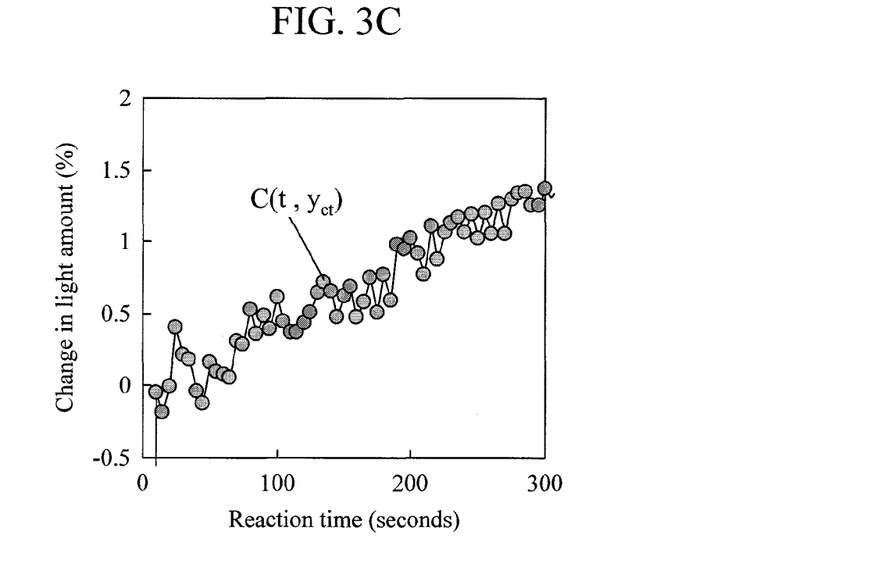
FIG. 3C is a chart showing reaction process data after data processing with respect to Embodiment 1.

Reaction process data for a latex agglutination reaction measured by the two photoreceivers 33a and 33b of the present embodiment are shown in FIG. 3A and FIG. 3B. FIG. 3A is a chart showing reaction process data $A(t, y_{at})$ by the main angle photoreceiver 33a disposed at a scattering angle of 20° and its fitting function $f_a(t)$. FIG. 3B is a chart showing reaction process data $B(t, y_{bt})$ by the sub-angle photoreceiver 33b disposed at a scattering angle of 30° and its fitting function $f_b(t)$. In FIG. 3B, there is also shown residual error $r_b(t)$, which is the difference between reaction process data $B(t, y_{bt})$ and its fitting function $f_b(t)$ at reaction time t. In addition, noise corrected reaction process data $C(t, y_{ct})$ after data processing is shown in FIG. 3C. The vertical axis of the reaction process data represents the change in light amount (%), which is the proportion of the difference between light amounts at a given time and 45 seconds after the introduction of the latex reagent, where the light amount after 45 seconds is taken to be 100%. The horizontal axis represents the time elapsed since the introduction of the latex reagent.

Assuming fitting function $f_a(t)$ of the main angle photoreceiver's reaction process data $A(t, y_{at})$ shown in FIG. 3A is $f_a(t)=at+b$, and that fitting function $f_b(t)$ of the sub-angle photoreceiver's reaction process data $B(t, y_{bt})$ shown in FIG. 3B is $f_b(t)=ct+d$, sensitivity ratio α between the main angle photoreceiver and the sub-angle photoreceiver is given by $\alpha=a/c$. Data obtained by subtracting estimated noise $n(t)$, which is estimated based on reaction process data $B(t, y_{bt})$ of the sub-angle photoreceiver, is shown in FIG. 3C as noise corrected reaction process data $C(t, y_{ct})$ that has undergone data processing. For cases where, as in the present embodiment, fitting function $f_b(t)$ of $B(t, y_{bt})$ is the linear equation $f_b(t)=ct+d$, data value $y_{ct}$ of noise corrected reaction process data $C(t, y_{ct})$ after data processing is given by the following.

$$y_{ct}=y_{at}-\alpha\{y_{bt}-(ct+d)\}$$

Thus, whereas the standard deviation among data values of the main angle photoreceiver's reaction process data shown in FIG. 3A taken over a period of one minute was 0.1%, the standard deviation among data values taken over a period of one minute dropped to about seven tenths thereof, i.e., to 0.07%, for the data processed reaction process data shown in FIG. 3C, thereby achieving enhanced sensitivity.

Embodiment 2

For the present embodiment, a method is described where a first photoreceiver is disposed at a position for receiving scattering light with a scattering angle of 20°, a second photoreceiver is disposed at a transmitted light receiving position (0°-scattering angle), and signals are amplified using reaction process data of these two photoreceivers when transmitted light is received. The device configuration is otherwise similar to that of Embodiment 1. In addition, the position of the first photoreceiver is not limited to a position for receiving scattering light with a scattering angle of 20°. It need only be disposed generally at a position for receiving scattering light whose scattering angle is greater than 0° but equal to or less than 35°, depending on the component being analyzed or the reaction type.

Figure 4A:
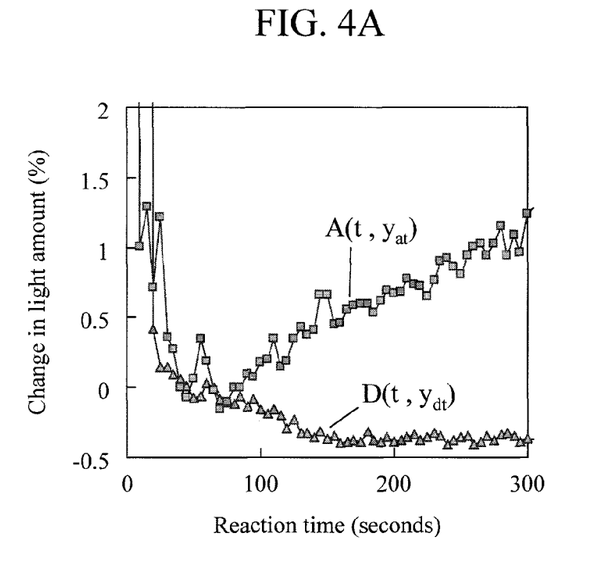
FIG. 4A is a chart showing reaction process data for each photoreceiver with respect to Embodiment 2.
Figure 4B:
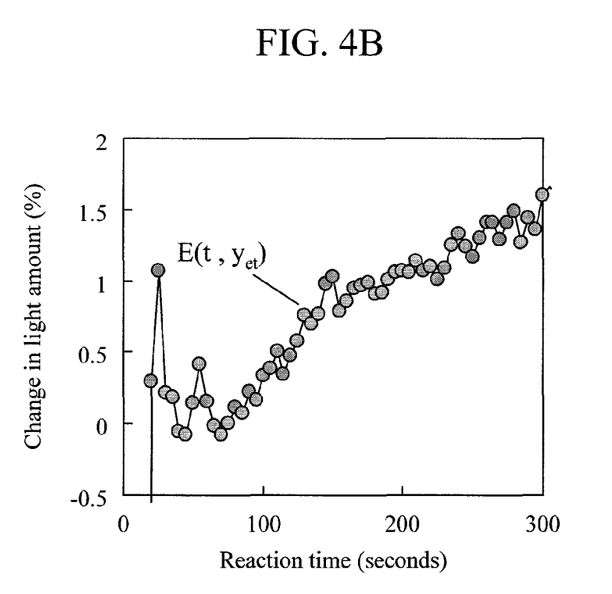
FIG. 4B is a chart showing reaction process data after data processing with respect to Embodiment 2.

Reaction process data $A(t, y_{at})$ of the first photoreceiver and reaction process data $D(t, y_{dt})$ of the second photoreceiver are shown in FIG. 4A. Transmitted light corrected reaction process data $E(t, y_{et})$ after data processing, which is obtained by determining the difference between reaction process data $A(t, y_{at})$ and reaction process data $D(t, y_{dt})$, is shown in FIG. 4B. Data value $y_{et}$ of transmitted light corrected reaction process data $E(t, y_{et})$ is calculated based on $y_{at}$ and $y_{dt}$ as in the following equation.

$$y_{et}=y_{at}-y_{dt}$$

Whereas the gradient of fitting function $f_a(t)$ of reaction process data $A(t, y_{at})$ was 0.4%/minute, the gradient of fitting function $f_e(t)$ of transmitted light corrected reaction process data $E(t, y_{et})$ after data processing rose to 0.6%/minute. Since the change in light amount thus becomes greater, precision improves. In addition, since the present embodiment uses as a base the reaction process data of transmitted light, which provides greater light amounts, it is possible to achieve enhanced sensitivity while keeping noise low.

REFERENCE SIGNS LIST

1 Sample
2 Sample cup
3 Sample disk
4 Reagent
5 Reagent bottle
6 Reagent disk
7 Reaction solution
8 Cell
9 Cell disk
10 Sample dispensing mechanism
11 Reagent dispensing mechanism
12 Stirring unit
13 Transmitted light measuring unit
14 Washing unit
17 Constant temperature fluid
31 Scattering light measuring unit
32 Transmitted light photoreceiver
33a, 33b Scattering light photoreceiver
34a, 34b Scattering light
35 Light source
36 Irradiating light
37 Transmitted light

The invention claimed is:

1. An auto analyzer comprising:
a disk having a plurality of cells formed in the disk, along the circumference thereof, wherein a cell contains a reaction solution in which a sample and a reagent are mixed;
a drive unit, constructed to alternate the disk between a rotating state and a stationary state;
a control unit, constructed to control the drive unit by use of signals sent to the drive unit;
a light measuring unit, including a light source, an analysis unit, a first photoreceiver, and a second photoreceiver; and
a data storage unit, constructed to store data from an input unit, data from the first and second photoreceivers, and calibration curve data, wherein a subset of the stored data is used by the control unit for control of the drive unit, and/or used by the analysis unit, and/or outputted to an output unit;
wherein the light measuring unit is constructed to irradiate the cell with irradiating light from the light source while the disk is rotating, and to measure light that has interacted with the reaction solution in the cell;
wherein the first and second photoreceivers are disposed such that the first photoreceiver is disposed to receive scattered light emanating from the reaction solution, that has a trajectory closer to an optical axis of the irradiating light than light received by the second photoreceiver, wherein the optical axis extends linearly from the light source through the reaction solution;
wherein the analysis unit is constructed to measure reaction process data, including changes in the amounts of light received by the first and second photoreceivers, and
wherein the analysis unit is constructed to determine an amount of a component in the reaction solution, by using data ($y_{ct}$) obtained by subtracting noise ($n(t)$) from reaction process data of the first photoreceiver ($y_{at}$), as follows:

$$y_{ct}=y_{at}-n(t);$$

wherein the analysis unit is constructed to estimate the noise ($n(t)$) by multiplying a sensitivity ratio ($\alpha$), between the first photoreceiver and the second photoreceiver to a residual error ($r_b(t)$), as follows:

$$n(t)=\alpha*r_b(t);$$

and wherein the analysis unit is constructed to estimate the residual error ($r_b(t)$) by calculating a difference between reaction process data of the second photoreceiver ($y_{bt}$) and a fitting function ($f_b(t)$) configured to fit reaction process data of the second photoreceiver, as follows:

$$r_b(t)=y_{bt}-f_b(t).$$

2. The auto analyzer according to claim 1, wherein both the first photoreceiver and the second photoreceiver are disposed at positions for receiving scattered light whose scattered angles are greater than 0° from the optical axis but equal to or less than 35° from the optical axis.

3. The auto analyzer according to claim 1, wherein the fitting function comprises a linear function.

4. The auto analyzer according to claim 1,
wherein the sensitivity ratio ($\alpha$), between the first photoreceiver and the second photoreceiver is a ratio of gradients $f_a'(t)$ to $f_b'(t)$ of fitting functions $f_a(t)$ and $f_b(t)$, respectively, as follows:

$\alpha = f_a'(t)/f_b'(t);$ wherein fitting functions $f_a(t)$ and $f_b(t)$ are fitting functions of reaction process data of the first photoreceiver and second photoreceiver, respectively.

* * * * *